(12) United States Patent
Hoeck et al.

(10) Patent No.: US 6,402,751 B1
(45) Date of Patent: *Jun. 11, 2002

(54) DEVICE FOR LINKING ADJACENT RODS IN SPINAL INSTRUMENTATION

(75) Inventors: James Van Hoeck, Cordova, TN (US); Denis S. Drummond, Narberth, PA (US); David L. Brumfield, Southhaven, MS (US); M. Neil Anderson; Michael C. Sherman, both of Memphis, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/613,406

(22) Filed: Jul. 11, 2000

Related U.S. Application Data

(63) Continuation of application No. 09/495,977, filed on Feb. 2, 2000, now Pat. No. 6,136,003, which is a division of application No. 08/946,955, filed on Oct. 8, 1997, now Pat. No. 6,113,600, which is a continuation of application No. 08/469,222, filed on Jun. 6, 1995, now abandoned.

(51) Int. Cl.[7] .............................................. A61B 17/58
(52) U.S. Cl. .......................................... 606/61; 606/72
(58) Field of Search .............................. 606/61, 72, 60, 606/69, 70, 71, 73; 623/17.11, 17.15

(56) References Cited

U.S. PATENT DOCUMENTS

| 2,638,301 A | 5/1953 | Smith |
| 3,499,222 A | 3/1970 | Linkow et al. |
| 4,641,636 A | 2/1987 | Cotrel ........................ 128/69 |
| 4,773,402 A | 9/1988 | Asher et al. ................. 128/69 |
| 4,957,495 A | 9/1990 | Kluger ........................ 606/58 |
| 5,002,542 A | 3/1991 | Frigg ........................... 606/61 |

(List continued on next page.)

FOREIGN PATENT DOCUMENTS

| DE | 32 19 575 A1 | 12/1983 |
| DE | 43 30 837 A1 | 3/1995 |
| EP | 0 446 092 | 2/1991 |
| FR | 2 645 427 | 4/1989 |
| FR | 2 714 590 | 7/1995 |
| GB | 2 208 476 | 4/1989 |
| WO | WO90/04948 | 5/1990 |
| WO | WO 95/13754 | 5/1995 |

OTHER PUBLICATIONS

*TSRH Crosslink Components*, Danek Medical, Inc., 1990.
*TSRH Crosslink*, Danek Medical, Inc., 1987.

*Primary Examiner*—Pedro Philogene
(74) *Attorney, Agent, or Firm*—Woodward, Emhardt, Naughton Moriarty & McNett

(57) ABSTRACT

One embodiment of a spinal fixation system 10 including a pair of longitudinal members 11, 12 positionable adjacent the spine, means for engaging longitudinal members to the spine 13, 14, a pair of wedge members 16 each having a bearing surface 38 configured to bear on a longitudinal member 11, 12, and a connector 20 configured to span a distance between the longitudinal members 11, 12. The connector 20 includes a pair of engaging members 25, 26 each having a fixation surface 33 and a connecting surface 30, and a bridge member 21 attached to the connecting surfaces 30. The engaging members 25, 26 each define a thru-hole 35 for receiving one of the wedge members 16. The thru-holes 35 are aligned so that wherein one of the wedge members 16 is advanced through the thru-hole 35, the bearing surface 38 will bear on a corresponding longitudinal member 11, 12 to force the longitudinal member 11, 12 into contact with the fixation surface 33 and engage the longitudinal member 11, 12 to the connector 20.

24 Claims, 11 Drawing Sheets

U.S. PATENT DOCUMENTS

| | | | |
|---|---|---|---|
| 5,005,562 A | 4/1991 | Cotrel | 128/69 |
| 5,024,213 A | 6/1991 | Asher et al. | 128/69 |
| 5,030,220 A | 7/1991 | Howland | 606/61 |
| 5,102,412 A | 4/1992 | Rogozinski | 606/61 |
| 5,129,900 A | 7/1992 | Asher et al. | 606/61 |
| 5,133,716 A | 7/1992 | Plaza | 606/61 |
| 5,147,359 A | 9/1992 | Cozad et al. | 606/61 |
| 5,147,360 A | 9/1992 | Dubousset | 606/61 |
| 5,154,718 A | 10/1992 | Cozad et al. | 606/61 |
| 5,275,600 A | 1/1994 | Allard et al. | 606/61 |
| 5,312,405 A | 5/1994 | Korotko et al. | 606/61 |
| 5,330,473 A | 7/1994 | Howland | 606/61 |
| 5,334,203 A | 8/1994 | Wagner | 606/61 |
| 5,368,594 A | 11/1994 | Martin et al. | 606/61 |
| 5,403,316 A | 4/1995 | Ashman | 606/61 |
| 5,439,463 A | 8/1995 | Lin | 606/61 |
| 5,522,816 A * | 6/1996 | Dinello et al. | 606/61 |
| 5,569,246 A * | 10/1996 | Ojima et al. | 606/61 |
| 5,601,552 A | 2/1997 | Cotrel | 606/61 |
| 5,624,442 A | 4/1997 | Mellinger et al. | 606/61 |
| 5,630,816 A | 5/1997 | Kamblin | 606/61 |
| 5,713,900 A | 2/1998 | Benzel et al. | 606/61 |
| 5,752,955 A * | 5/1998 | Errico | 606/61 |
| 5,843,082 A * | 12/1998 | Yuan et al. | 606/61 |
| 5,980,523 A * | 11/1999 | Jackson | 606/61 |
| 6,136,003 A * | 10/2000 | Hoeck et al. | 606/61 |

* cited by examiner

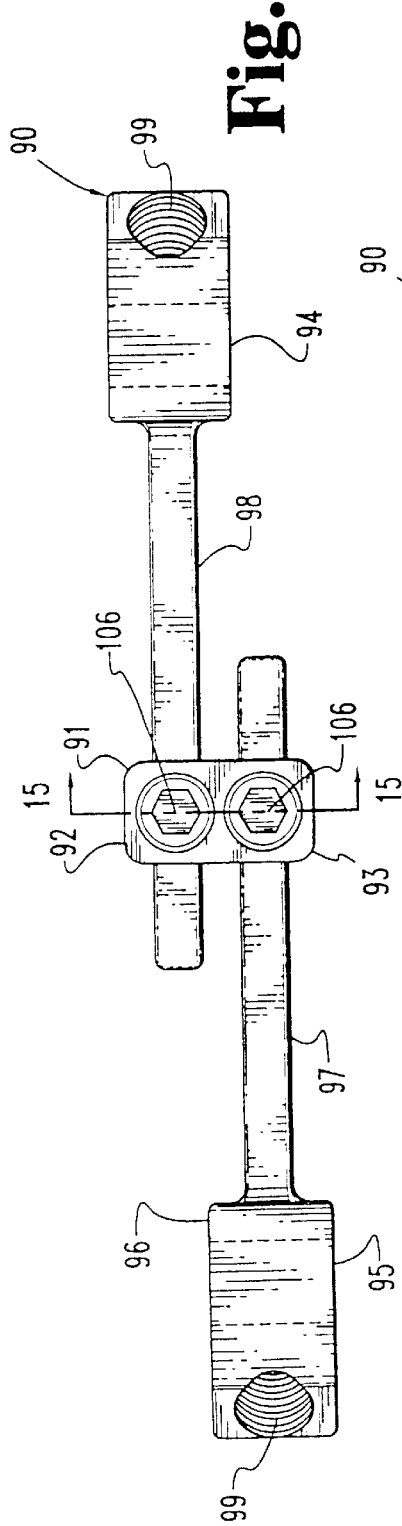
Fig. 13
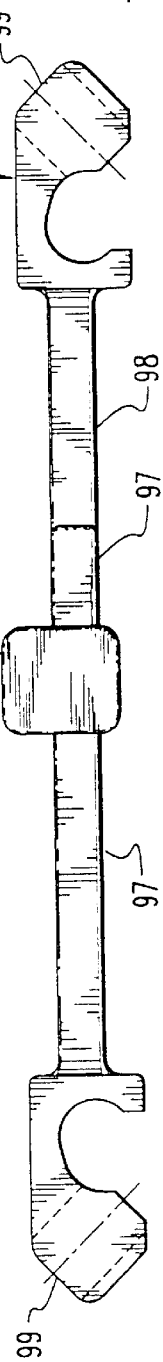
Fig. 14
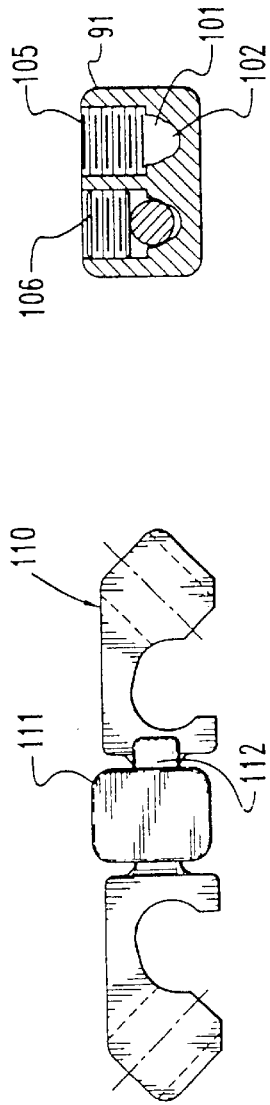
Fig. 15
Fig. 18

DEVICE FOR LINKING ADJACENT RODS IN SPINAL INSTRUMENTATION

This application is a continuation of U.S. patent application Ser. No. 09/495,977, filed on Feb. 2, 2000 now U.S. Pat. No. 6,136,003, which is a divisional application of pending U.S. patent application Ser. No. 08/946,955, filed on Oct. 8, 1997 now U.S. Pat. No. 6,113,600, which is a file wrapper continuation of U.S. patent application Ser. No. 08/469,222, filed on Jun. 6, 1995, now abandoned, the contents of which are incorporated herein by reference.

FIELD OF THE INVENTION

The present invention broadly concerns devices for use in spinal implant systems, particularly those using spinal rods contoured for connection at various locations along the length of the spinal column. More specifically, the invention concerns an apparatus for linking adjacent spinal rods in a top-loading and top-tightening fashion. This invention is particularly useful with methods and devices for posterior fixation of the spine.

BACKGROUND OF THE INVENTION

Several techniques and systems have been developed for use in correcting and stabilizing spinal curvatures, and for facilitating spinal fusion in the case of spinal disorders or degenerative conditions. Typically, a pair of bendable rods are longitudinally disposed adjacent the vertebral column and are fixed to various vertebrae along the length of the spine by way of a number of fixation elements, such as hooks and screws.

Numerous spinal rod systems have been developed which provide transverse connectors for linking the adjacent spinal rods across the spinal midline to provide a rigid and stable construct. Most of these systems present one or more difficulties for spinal surgeons. Many of the devices are high profile which increases soft tissue trauma and surgical complications. Furthermore, in many of these prior systems the attachment mechanisms must be preloaded on the spinal rods which can require significant pre-operative planning and which virtually eliminates the opportunity to add connectors in situ.

One transverse connector system is the TSRH® CROSSLINK® of Danek Medical, Inc. The TSRH® CROSSLINK® utilizes a three point shear clamp mechanism which restricts motion between the rods in all directions, and particularly resists axial forces between rods and torsional moments about the axis of the rods. A quadrilateral construct is formed by laterally connecting the rods across the sagittal plane with rigid plates. The lateral connection reduces the loss of correction that can occur over time.

Rigid transverse connections between spinal rods are beneficial because they restrict rod migration and increase construct stiffness. In many cases involving multi-level fusion of the spine, these features are essential while solid bone fusion is accomplished. In the post-operative period before fusion occurs, a significant amount of motion can occur between the rods, wires and hooks, which can, for example, allow a scoliotic correction to decrease or the pelvis to de-rotate toward its previous, deformed position. By providing a rigid transverse connection between two spinal rods, the loss of correction can be reduced and a stiffer construct can be created which may enhance the promotion of a solid fusion. While the TSRH® CROSSLINK® provides an excellent construct, a need has remained for low profile devices which link adjacent spinal rods in a top-loading and top-tightening fashion with a minimum of components and steps.

SUMMARY OF THE INVENTION

In accordance with one aspect of the invention, a connector is provided for linking adjacent longitudinal members, such as spinal rods, engaged to a spine. The apparatus includes a bridge member sized to span at least a portion of the distance between the spinal rods. A pair of engaging members are connected to the bridge member, each including a receptacle configured to receive a longitudinal member- when the connector is disposed over the adjacent rods. The engaging members also include the fixation surface adjacent to the receptacle and configured for engaging a longitudinal member, and a thru-hole defined in the engaging member adjacent to the receptacle for receiving a wedge member. The thru-hole intersects the receptacle and is aligned at an angle such that as the wedge member is advanced through the thru-hole, the wedge member will bear against a rod initially disposed in the receptacle and push the rod against the fixation surface to engage the connector to the rod.

In one specific embodiment of the invention, the engaging members include elongated connecting portion which are received by a bore in the bridge member. The bridge member also includes a pair of engaging surfaces adjacent to and contiguous with a respective one of the bores for engaging a connecting portion. A second thru-hole defined in the bridge member intersects each one of the bores and is aligned at an angle such that as a wedge member is advanced through the second thru-hole, the wedge member will bear against the connecting portions and push each one against a corresponding one of the engaging surfaces.

In another specific embodiment, the bridge member defines a slot for receiving one of the connecting portions and a first fastener bore which intersects the slot. The connecting portion also defines a second fastener bore which is alignable with the first fastener bore of the bridge member when the connecting portion is inserted into the slot.

In some embodiments of this invention, the fixation surface includes a circular concavity which has a smaller radius than the radius of the longitudinal member. This provides three points of contact on each of the longitudinal members which restricts motion between the rods in all directions.

One object of the invention is to provide an apparatus for use in laterally connecting longitudinal members implanted adjacent a patient's vertebral column. Another object of this invention is to provide an apparatus which restricts rod migration and increases overall construct rigidity.

One advantage of this invention is that it provides fixation assemblies that can be top loaded, or implanted over spinal rods after the spinal rods have been engaged to the spinal column. A further benefit is achieved by top-tightening aspects of the invention.

Another benefit of this invention is that it provides three points of contact on the spinal rod which restricts rod migration and increases overall construct rigidity.

Other objects and further benefits of the present invention will become apparent to persons of ordinary skill in the art from the following written description and accompanying figures.

BRIEF DESCRIPTION OF THE DRAWINGS

FIG. 13 is a top elevational view of an adjustable transverse connector.

FIG. 14 is a side elevational view of the transverse connector of FIG. 13.

FIG. 15 is a cross-sectional view of the connector of FIG. 13 taken along lines 15—15.

FIG. 18 is a side elevational view of an alternative embodiment of the transverse connector having shortened connecting portions.

DESCRIPTION OF THE PREFERRED EMBODIMENTS

Figure 1:
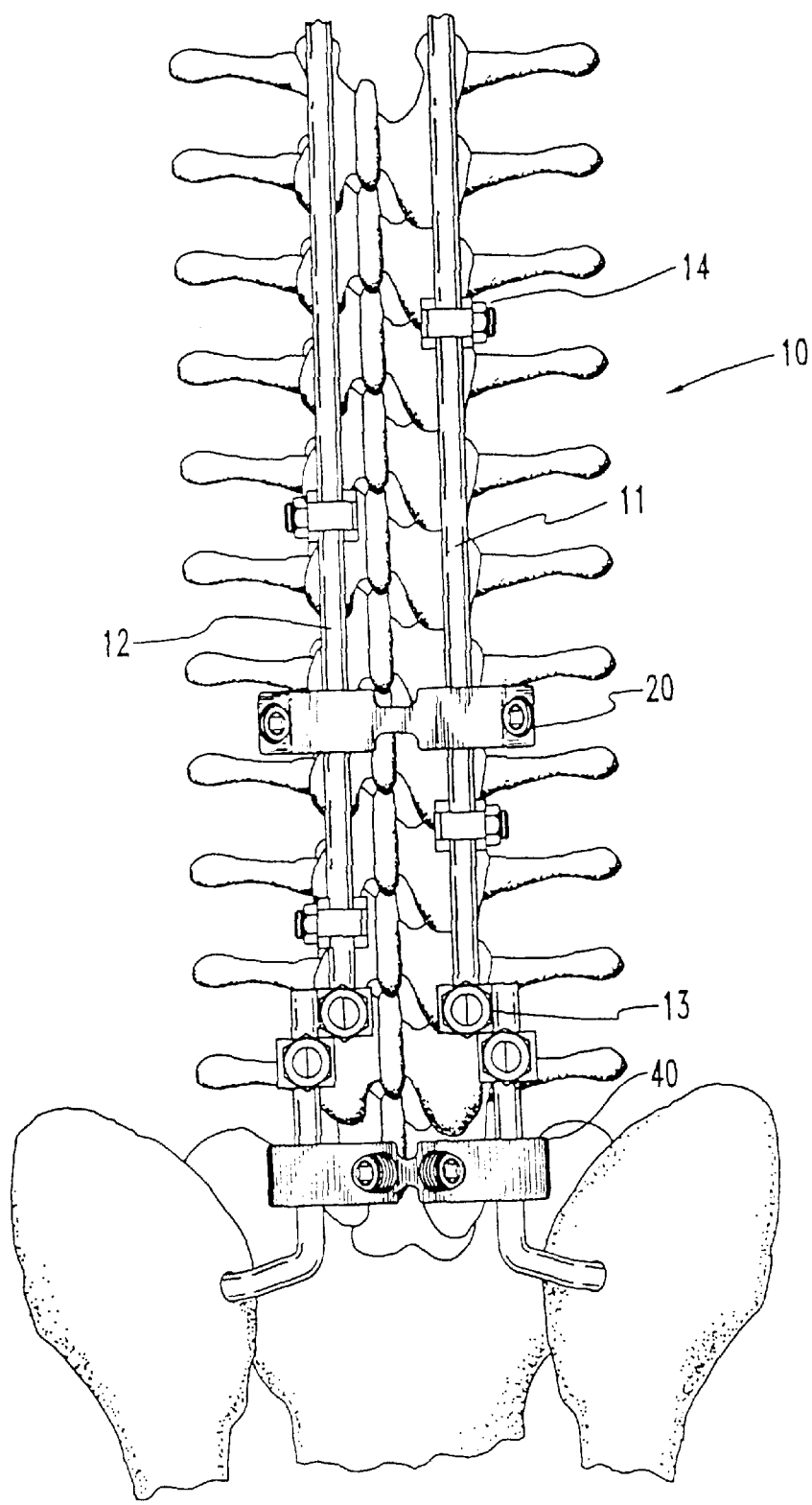
FIG. 1 is a top elevational view of a spinal fixation system engaged to a spine according to one aspect of this invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention is useful for posterior internal fixation of the spine which is indicated for correcting and stabilizing spinal curvatures and for facilitating spinal fusion in the case of spinal disorders or degenerative conditions. This invention provides a top-loaded, top-tightening, low profile posterior fixation system which requires minimal instrumentation yet provides a stable, rigid quadrilateral construct that restricts rod migration and increases overall construct rigidity.

Figure 2:
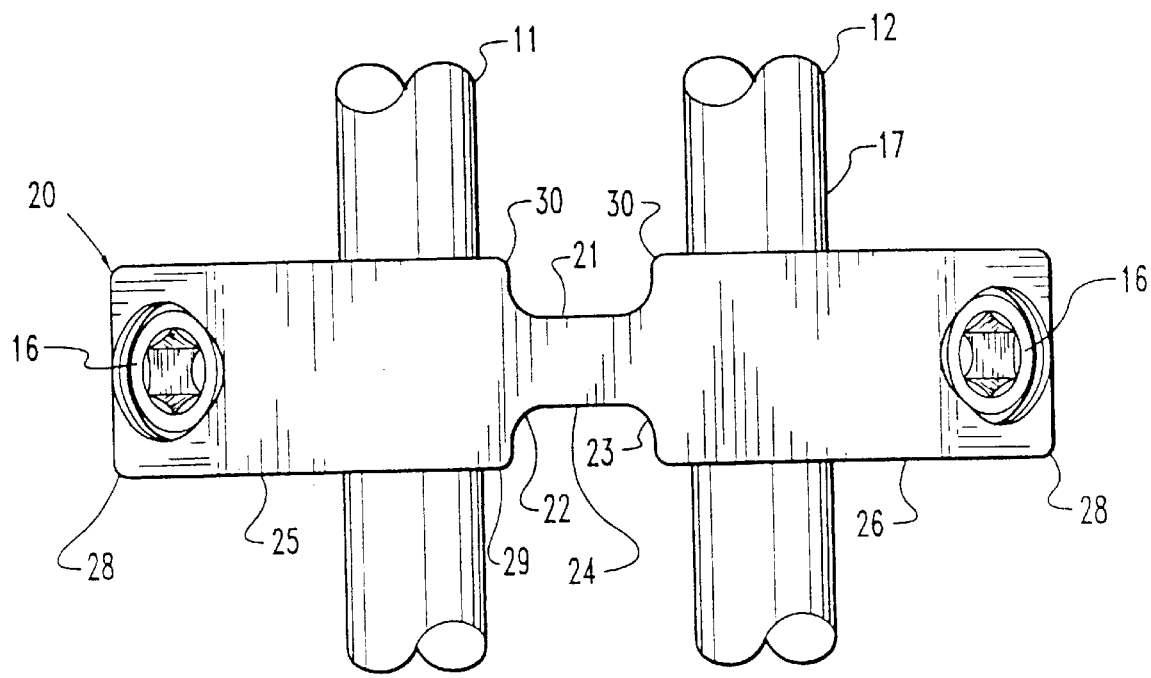
FIG. 2 is a top elevational view of a transverse connector engaged to spinal rods wherein the engaging members are disposed medially and the thru-holes are disposed laterally on the connector.
Figure 3:
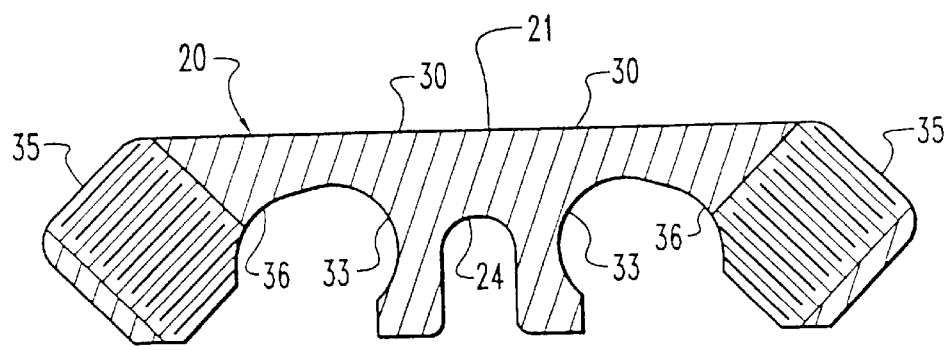
FIG. 3 is a cross-section of the transverse connector of FIG. 2.

A spinal fixation system 10 in accordance with one preferred embodiment of the present invention is depicted in FIGS. 1–3. The system 10 includes a pair of longitudinal members, preferably spinal rods, 11,12 means for engaging the longitudinal members to the vertebral column, 13, 14, a pair of wedge members 16 and a connector 20 configured to span a distance between the rods 11, 12 when the rods 11, 12 are engaged to the spine.

As shown more clearly in FIGS. 2 and 3, the connector 20 includes a pair of engaging members 25, 26 each defining a fixation surface 33 at a corresponding first end 28 thereof. The connector 20 also includes a connecting surface 30 at a second end 29 of each engaging member 25, 26. A bridge member 21 includes a first end 22 and a second end 23 which are attached to the connecting surfaces 30 of each of the rod engaging members 25, 26. The bridge member 21 preferably includes a reduced width and depth portion 24 to avoid the laminae and spinous process remnant during the surgical procedure. The reduced portion 24 also provides means for contouring or bending the connector 20 as needed to conform to the spinal anatomy of the patient.

Each of the engaging members 25, 26 further defines a receptable 36 for receiving a spinal rod therein and a first thru-hole 35 for receiving a wedge member 16. The thru-holes 35 intersect the corresponding receptacles 36 and are aligned so that when a wedge member 16 is advanced through the thru-hole 35, the wedge member 16 bears on a corresponding rod 11, 12 within a receptacle 36 to force the rod 11, 12 into contact with an opposite fixation surface 33 to engage the rod to the connector. In one specific embodiment, the engaging members 25, 26 are integrally attached to the bridge member 21.

One advantage of this invention is that it provides connectors that can be top loaded, or implanted over spinal rods after the spinal rods have been engaged to the vertebrae. Top-loading is advantageous because it reduces the required size of the surgical opening and resulting trauma to the patient, and because it greatly simplifies the surgical implantation. Top-loading also provides a mechanical advantage during implantation of the system in that the connector 20 can be easily placed over adjacent rods 11, 12 and then the rods 11, 12 can be locked laterally relative to each other by tightening the wedge members 16.

Figure 4:
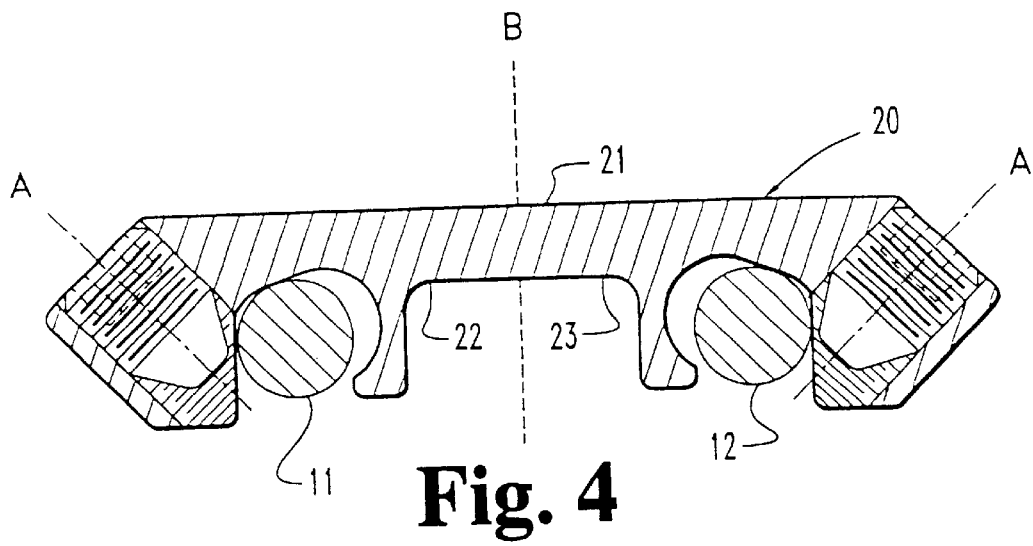
FIG. 4 is a cross-sectional view of the transverse connector of FIG. 2 which is top loaded over two spinal rods.
Figure 5:
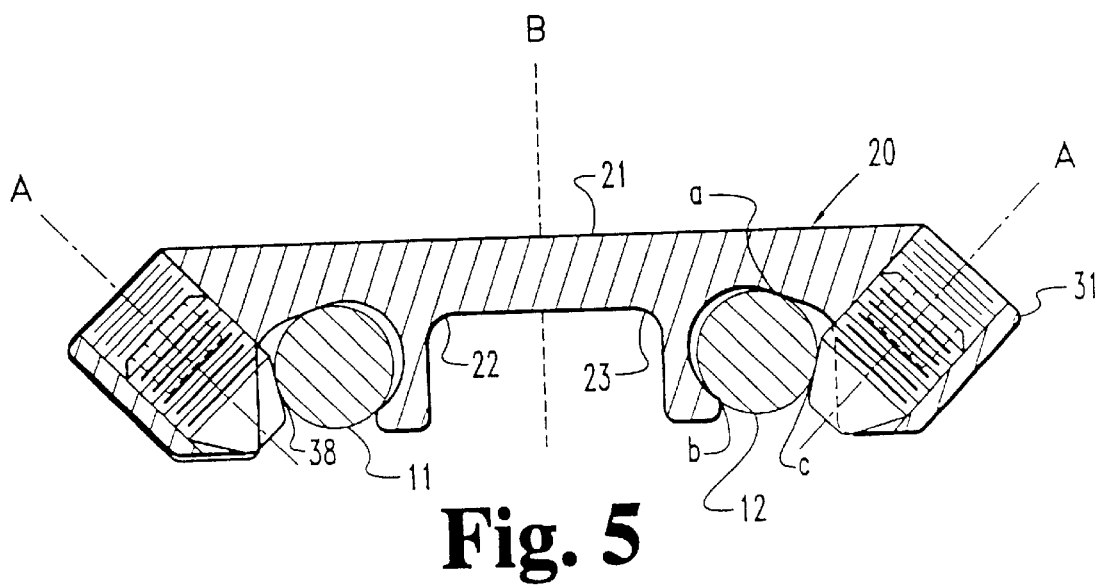
FIG. 5 is a cross-sectional view of the transverse connector of FIG. 2 engaged to two spinal rods.

Referring to FIGS. 3, 4 and 5, the connector 20 can be disposed or loaded over longitudinal members or rods 11, 12 which have been previously engaged to the spine such that the rods 11, 12 are received into the receptacle 36 of the connector 20. Then, as a wedge member 16 is advanced through a thru-hole 35, the wedge member 16 pushes the rod 11 against the fixation surface 33. Preferably, the fixation surface 33 is a circular concavity which has a smaller radius than the radius of the rod 11, 12. This configuration provides three points of contact a, b, c On the longitudinal members 11, 12 as shown in FIG. 5. Two Points of contact a and b are provided by the fixation surface 33, and the third point of contact c is provided by bearing surface 38 on the wedge member 16.

Figure 7:
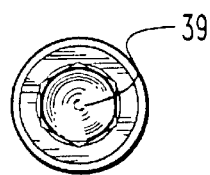
FIG. 7 is a top elevational view of a set screw.
Figure 6:
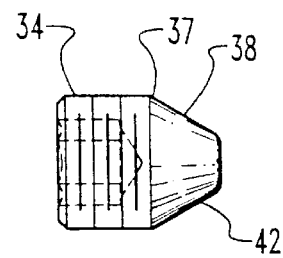
FIG. 6 is a side elevational view of a set screw.

As shown more clearly in FIGS. 6 and 7, the wedge member 16 is preferably a set screw 37 which has a bearing surface 38 and an internal hex 39 to accept a conventional driving tool. Most preferably, the head 34 of the wedge member 16 or set screw 37 is configured to rest entirely within the thru-hole 35. In this manner, the set screw 37 can be situated so that it does not extend above the upper surface 31 of the connector 20 when the set screw 37 is fully advanced in the thru-hole 35 and bearing against a rod 12 as shown in FIG. 5. In the case of a threaded set screw 37, the thru-holes 35 carry corresponding female threads. Preferably, bearing surface 38 is shaped to conform to an outer surface 17 of a rod 11, 12. The outer surface 17 of the rod 11, 12 is typically circular or circumferential but can be of any suitable shape. The bearing surface 38 is preferably a tapered tip 42.

Referring to FIGS. 2 through 5, the bridge members defines an axis B between the first end 22 and the second end 23 of the bridge member 21. The thru-holes 35 are preferably oriented at an angle A of less than 90° relative to the axis B of the bridge member 21. Any angle which allows the wedge member 16 to bear against a rod 11, 12 in the receptacle 36 and push the rod 1i, 12 against the fixation surface 33 so that the adjacent rods 11. 12 are retained in a desired special relationship are contemplated. Such angles include but are not limited to angles of about 40°, 45° and 60°. Preferably the angle is established to preserve the top-tightening aspect of the invention, which can help reduce the size of the surgical site for implantation.

Figure 8:
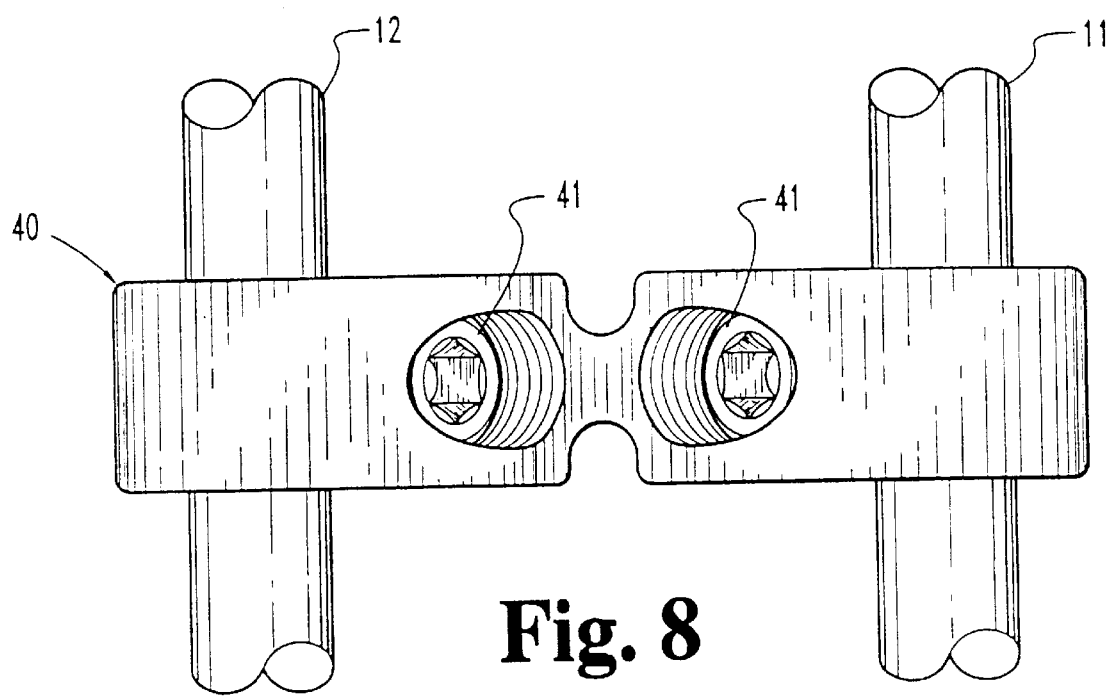
FIG. 8 is a top elevational view of a transverse connector similar to FIG. 1 except that the engaging members are disposed laterally and the thru-holes are disposed medially on the connector.
Figure 9:
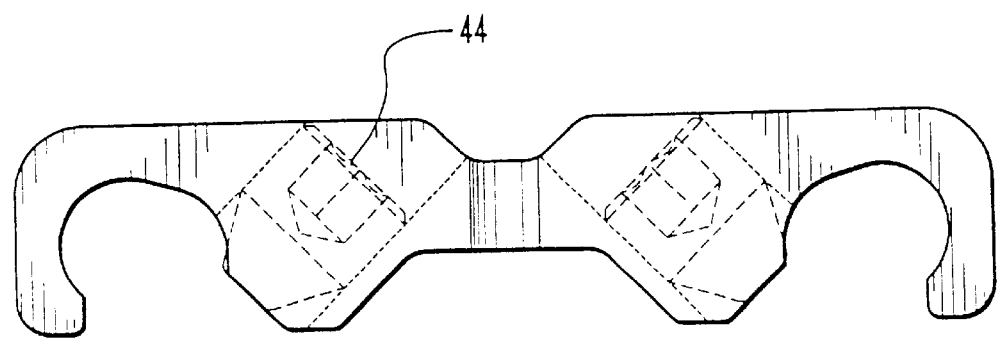
FIG. 9 is a side elevational view of the transverse connector of FIG. 8.

In the embodiments shown in FIGS. 1 through 5, the connector 20 includes thru-holes 35 which are disposed laterally on the connector, i.e., laterally outboard from the axis B. In this configuration the thru-holes 35, and therefore the wedge members 16, act toward the axis B. Alternatively, the first thru-holes 44 may be disposed medially on the connector 40, as shown in FIGS. 8 and 9. This embodiment is desirable when the span between the longitudinal members 11, 12 is sufficient to accommodate both wedge members 41. A transverse connector 20 which utilizes laterally disposed wedge members 16 such as depicted in FIGS. 1–5, can be used when the span between the longitudinal members 11 and 12 is smaller than about 1⅛" (28 mm). However, when appropriate, the medial connector embodiment 40 is desirable because it permits a smaller surgical site and allows easier access to the wedge members 41 with tools (not shown) for engaging the wedge member 41 during the surgical procedure.

Figure 10:
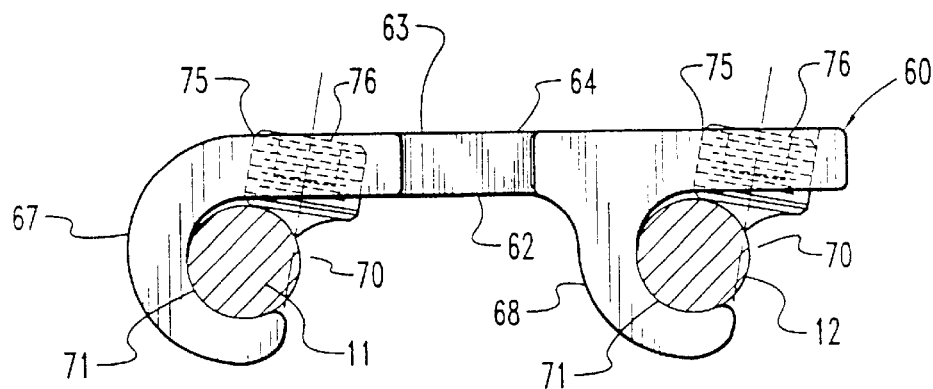
FIG. 10 is a side elevational view of an alternative embodiment of a transverse connector.

Referring to FIG. 10, this invention also contemplates a C-clamp shaped connector 60. The C-clamp connector 60 also includes a bridge member 62 which spans between a pair of engaging members 67, 68. The bridge member 62 is connected to each of the engaging members 67, 68 at a first end 63 and a second end 64 of the bridge member 62. A pair of receptacles 70 on the connector 60 are configured to receive longitudinal members or rods 11, 12. A first thru-hole 75 is defined in each of the engaging members 67, 68. The thru-holes 75 intersect the corresponding receptacles 70 and are aligned at an angle such that as a wedge member 76 is advanced through the thru-hole 75, the wedge member 76 will bear against the longitudinal member 11, 12 and push the longitudinal member 11, 12 against a fixation surface 71 adjacent to the corresponding receptacles 70 to engage the connector 60 to a longitudinal member 11, 12. Like the previous embodiments, the connector 60 can be loaded over a pair of spinal rods 11, 12, with the rods 11, 12 initially in contact with only the receptacles 70 or the underside of the connector 60. The connector can be manually shifted until the rods contact the fixation surfaces 72. Final engagement is accomplished by tightening the wedge members 76 against the rods.

Figure 11:
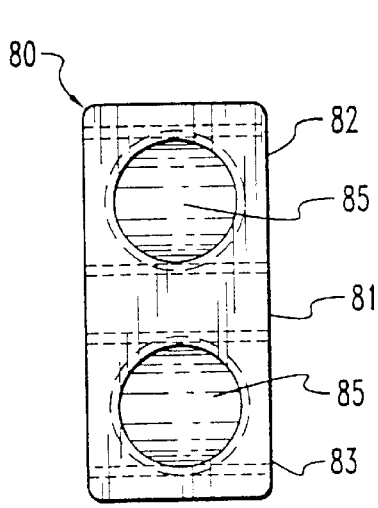
FIG. 11 is a top elevational view of a closed transverse connector embodiment.
Figure 12:
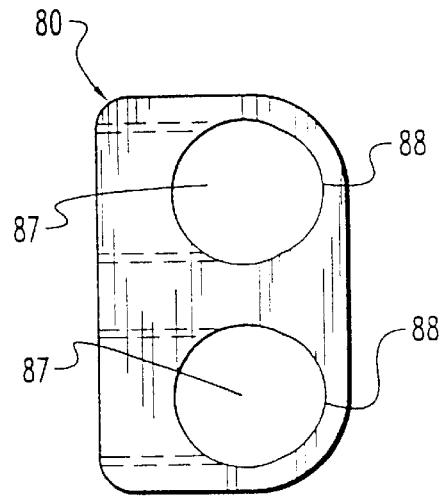
FIG. 12 is a side elevational view of the transverse connector of FIG. 11.

Closed connector embodiments are also contemplated by this invention as shown in FIGS. 11 and 12. The closed connector 80 must be preloaded on the longitudinal members 11, 12 before the longitudinal members 11, 12 are engaged to a spinal column. The closed connector 80 includes a bridge member 81 attached to a pair of engaging members 82, 83. A pair of rod receptacles 87 are configured to receive a longitudinal member 11, 12. A first thru-hole 85 is defined in each engaging member 82, 83 for receiving a wedge member 16. As the wedge member 16 is advanced through the thru-hole 85, the wedge member 16 will bear against a longitudinal member 11, 12 in the receptacle 87 and push the longitudinal member 11, 12 against a fixation surface 88 to engage the connector 80 to the longitudinal member 11, 12. Preferably the fixation surface 88 is a circular concavity which has a smaller radius than the radius of the longitudinal member 11, 12, thus providing three points of contact as described above.

Another aspect of this invention provides means for adjusting the distance between the longitudinal members 11, 12 while still retaining the top-loaded and top-tightening aspects of the invention. FIGS. 13 and 14 show an adjustable transverse connector 90. The connector 90 includes a bridge member 91 having a first end 92, a second end 93 and engaging members 94, 95. The engaging members 94, 95 each include an engaging portion 96 which define thru-holes 99 and which are engageable to the longitudinal members 11, 12 as described above. Each engaging member 94, 95 also includes elongated connecting portions 97, 98 sized to span at least a portion of the distance between the adjacent longitudinal members or rods 11, 12. The bridge member 91 defines a pair of bores 101, each for receiving a corresponding one of the elongated connecting portions 97, 98. The bridge member also includes a pair of engaging surfaces 102 which are adjacent to and contiguous with a respective one of the bores 101 for engaging the corresponding connecting portions 97,98, as shown in FIG. 15. A pair of second thru-holes 105 are defined in the bridge member 91 for receiving wedge members 106. A second thru-hole 105 intersects each of the bores 101 and is aligned at an angle such that as the wedge member 106 is advanced through the second thru-hole 105, the wedge member 106 will bear against the corresponding connecting portion 97, 98 and push each of the connecting portions 97, 98 against a corresponding one of the engaging surfaces 102. Preferably, the engaging surfaces 102 include a circular concavity which has a smaller radius than a radius of the bore 101 and of the circular connecting portions 97, 98.

Figure 16:
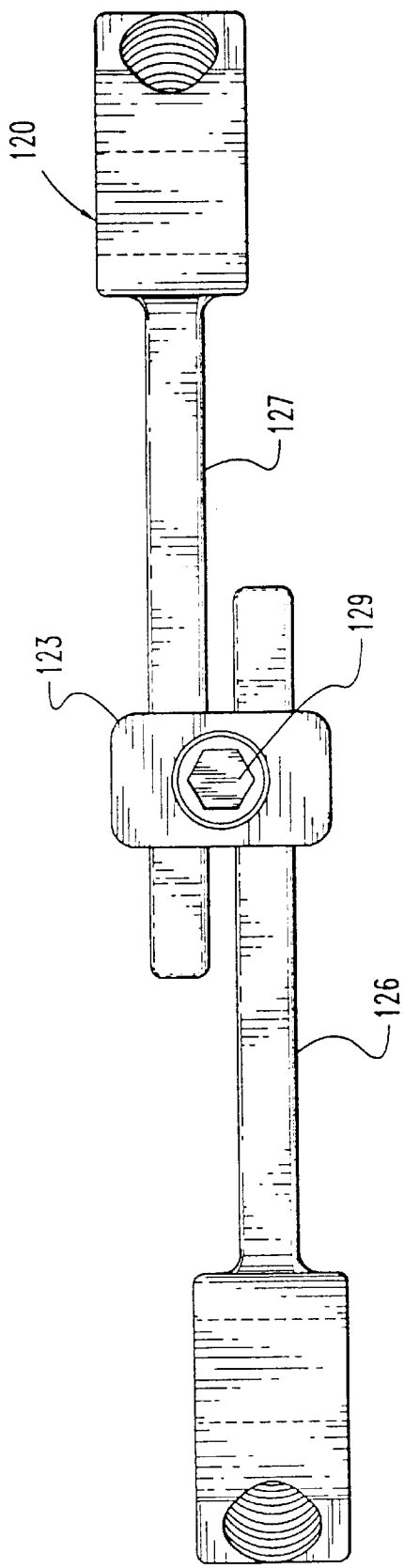
FIG. 16 is a top elevational view of another adjustable transverse connector.
Figure 17:
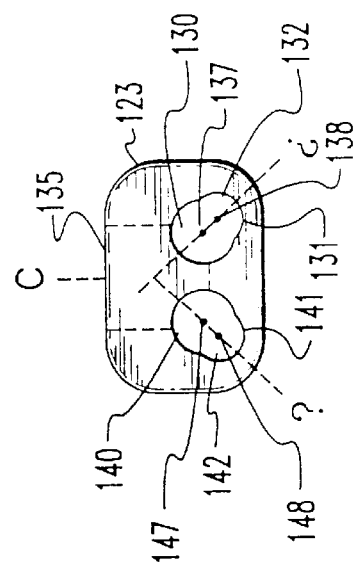
FIG. 17 is a side elevational view of the bridge member of the transverse connector shown in FIG. 16.

One preferred embodiment of an adjustable transverse connector 120 which is similar to the embodiment shown in FIGS. 13–15 is shown in FIGS. 16 and 17. A single second thru-hole 135 defined in the bridge member 123 intersects both of the bores 130, 140 so that a single wedge member 129 engages both of the connecting portions 126, 127 as shown in FIGS. 16 and 17. According to this embodiment, a single wedge member 129 forces the connecting portions 126 and 127 laterally into the respective engaging surfaces 131, 141. Each engaging surface 131, 141 includes a concavity 142, 132 which has a centroid 138, 148. As shown in FIG. 17, a line between the centroid 137 of a bore 130 and the centroid 138, of its corresponding adjacent concavity 132 and a line β between the centroid 147 of the other bore 140 and the centroid 148 of its corresponding adjacent concavity 142 diverge away from the second thru-hole 135. In this configuration, as the wedge member 129 is advanced through the second thru-hole 135 the connecting portions 126, 127 are pushed away from the axis C of the second thru-hole 135. The connecting portions 126, 127 are thus engaged to the corresponding engaging surfaces 131, 141 with a single wedge member 129.

In order to provide a broad range of connectors to address a variety of spinal situations and vertebral levels, connectors of various sizes are contemplated. For example,. the connector 110 shown in FIG. 18 provides shortened connecting portions 112 connected to a bridge member 111.

The invention also includes a telescoping adjustable transverse connector as shown in FIGS. 19 through 22. The telescoping adjustable transverse connector 150 includes a bridge member 152 connected to a first engaging member 155 and a second engaging member 162, each having a respective first end 156, 163 and second end 158, 165. The engaging members 155, 162 each include fixation portions 157, 164 at the first end 156, 163. The fixation portions 157, 164 each include receptacles 168, 169 and fixation surfaces 170, 171. The receptacles 168, 169 are each intersected with a first thru-hole 175. The fixation portions 157, 164 of the connector 150 are engageable to longitudinal members in a top loaded fashion in the manner described above.

The first engaging member 155 includes a first connecting portion 159 at the second end 158. The second engaging member 162 similarly includes a second connecting portion 166 at the second end 165. The bridge member 152 of the connector 150 defines a slot for receiving the second connecting portion 166. The first connecting portion 159 of the first engaging member 155 is preferably integrally attached to the bridge member 152. The bridge member 152 also defines a first fastener bore 177. The axis D of the first fastener bore 177 intersects the slot 153 for receiving a fastener 180. The second connecting portion 166 defines a second fastener bore 178. The second fastener bore 178 is alignable with the first fastener bore 177 when the second connecting portion 166 is inserted in the slot 153. A fastener 180 is extendable through each of the first and second fastener bores 177, 178 to clamp the second connecting portion 166 to the bridge member 152. Any suitable fastener is contemplated, including but not limited to a hex head screw 180 with an integral washer 181.

Figure 22:
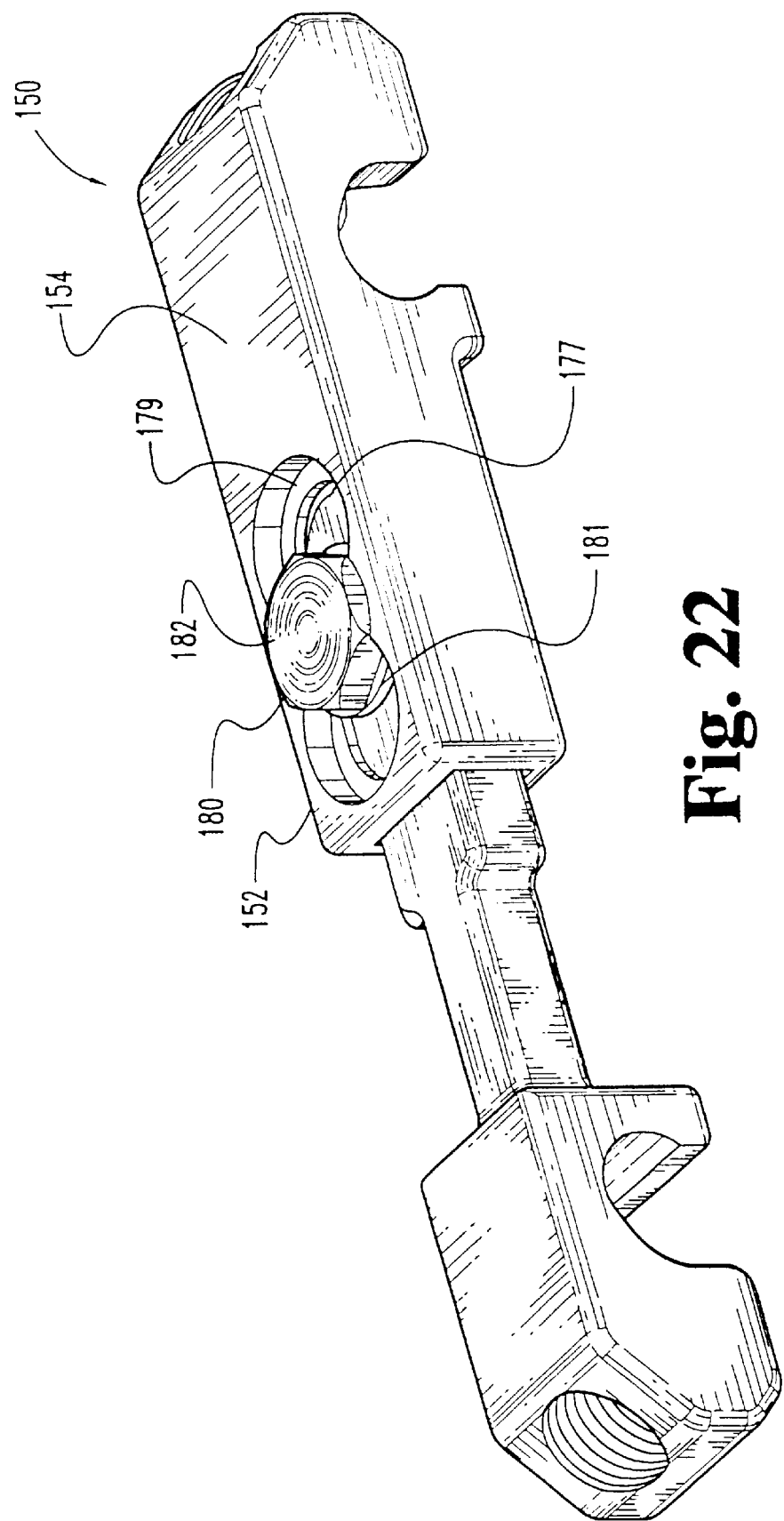
FIG. 22 is a perspective view of still another transverse connector of this invention.

Preferably, the first fastener bore 177 of the bridge member 152 includes a recess 179 defined in an upper surface 154 of the connector 150 as shown in FIG. 22. The head 182 and washer 181 of the fastener 180 are sized to be received within the recess 179 without extending above the upper surface 154 of the bridge member 152. This embodiment provides a low profile system. With this configuration it is contemplated that the fastener 180 can include a circular head with an internal hex recess to receive a driving tool.

Figure 19:
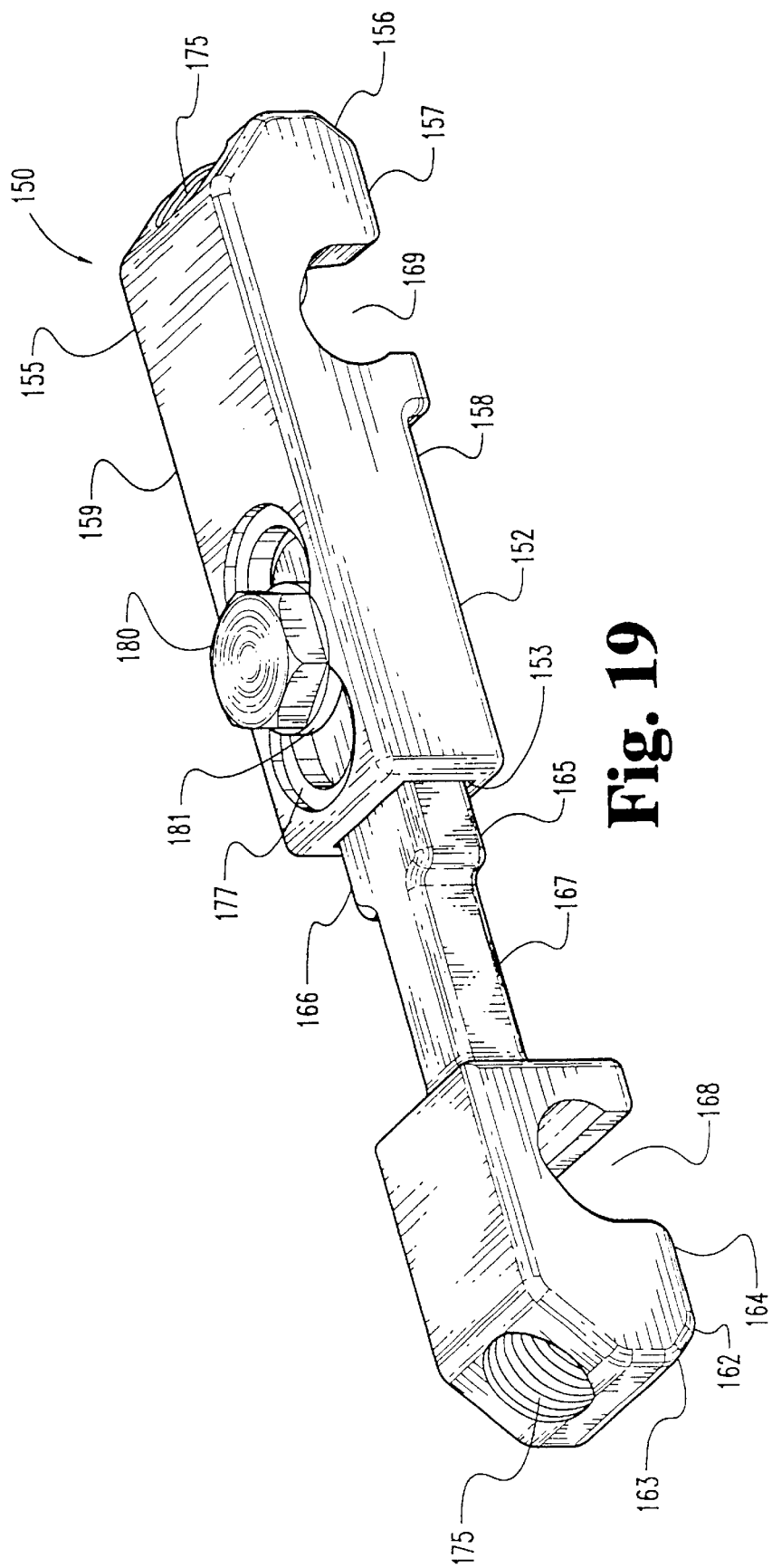
FIG. 19 is a perspective view of still another adjustable transverse connector according to this invention.
Figure 20:
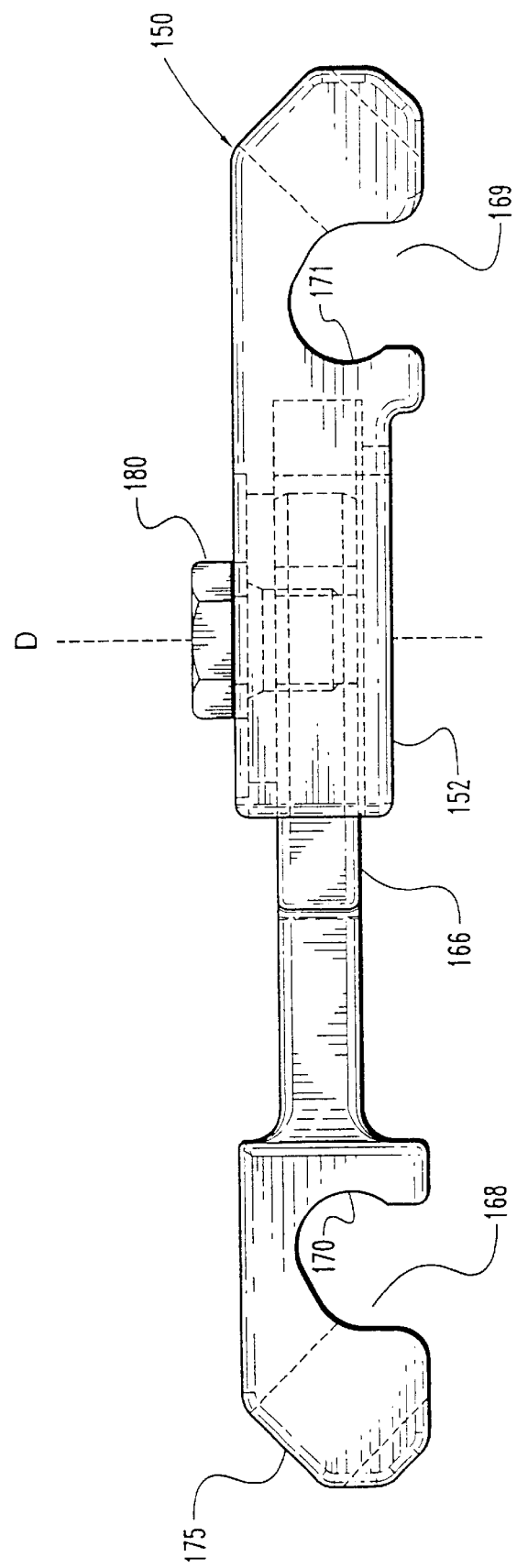
FIG. 20 is a side elevational view of the transverse connector shown in FIG. 19.
Figure 21:
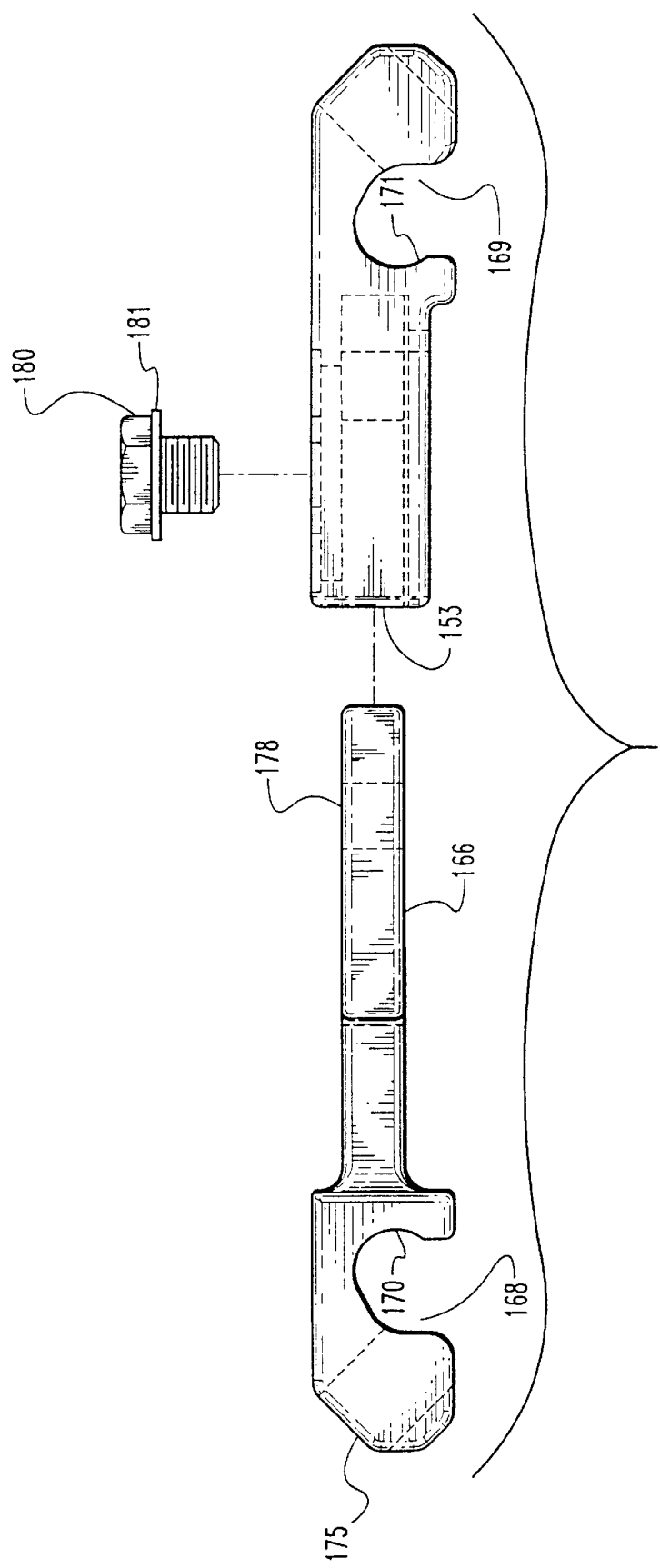
FIG. 21 is an exploded side view of the transverse connector of FIG. 19.

Preferably, as shown in FIG. 19, the bridge member 152 also includes a number of first fastener bores 177 and the second connecting portion 166 is slidable within the slot 153 so that the second fastener bore 178 is alignable with each of the number of first fastener bores 177. This configuration allows adjustability in the length of the connector 150. Preferably, the second connecting portion 166 includes an area of reduced width 167 for bending and contouring the connector 150.

The connectors and systems of this invention are preferably formed of medical grade stainless steel or similar high strength material. Other biocompatible materials are contemplated provided the material is strong enough to endure the high loads transmitted through the components. Specifically, the systems could be manufactured in 6A14V titanium or 316LVM stainless steel. The connectors can be provided in several different sizes as necessary to accommodate the spinal anatomy at the cervical, thoracic and lumbar segment of the spine.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed:

1. A device for transversly connecting a pair of longitudinal-members, comprising:
   a pair of engaging members adjustably linked by a bridge member, each of said engaging members including:
      a fixation surface adapted to engage a respective one of the longitudinal members thereon; and
      a thru-hole oriented at an oblique angle relative to an axis of the device extending transversely across the longitudinal members; and
   a pair of wedge members, each of said wedge members being operable to advance through said thru-hole to urge said respective one of the longitudinal members laterally relative to said wedge member and into engagement with said fixation surface.

2. The device of claim 1, wherein said pair of longitudinal members are spinal rods, said spinal rods being operably engaged to the spine and having relative positions and orientations conforming to the anatomy of the spin, said bridge member being adjustable to conform to said relative position and orientations of said spinal rods.

3. The device of claim 1, wherein said bridge member is adapted to provide adjustable length between said engaging members.

4. The device of claim 3, wherein said bridge member is operatively coupled to one of said engaging members and defines an opening sized to receive an elongated portion operatively coupled to another of said engaging members to provide said adjustable length between said pair of engaging members.

5. The device of claim 4, wherein said elongated portion is adapted to provide adjustment to conform to relative orientations of said longitudinal members.

6. The device of claim 3, wherein said bridge member is adjustable to conform to relative orientations of said longitudinal members.

7. The device of claim 6, wherein said bridge member includes a reduced cross sectional portion, said reduced cross sectional portion being deformable to conform to misalignments between said longitudinal members.

8. The device of claim 1, wherein said oblique angle in a range of about 40 to 60 degrees.

9. The device of claim 1, wherein said thru-hole is offset from said respective one of said longitudinal members when said respective one of said longitudinal members is engaged against said fixation surface.

10. The device of claim 1, wherein each of said wedge members has a curved bearing surface substantially complementary to an outer surface of said longitudinal members, said curved bearing surface contacting said outer surface to urge said respective one of the longitudinal members into engagement with said fixation surface.

11. The device of claim 1, wherein said thru-holes are disposed laterally on the device.

12. The device of claim 1, wherein said thru-holes are disposed medially on the device.

13. A spinal fixation system, comprising:
   a pair of longitudinal members operatively engaged to the spine; and
   an adjustable connector defining an axis extending transversely across said longitudinal members, said connector including:

a pair of engaging members linked by a bridge member, said bridge member being adapted to provide adjustable length between said engaging members, each of said engaging members including:
  a fixation surface adapted to engage a respective one of said longitudinal members thereon; and
  a thru-hole oriented at an oblique angle relative to the axis of said connector and offset from said respective one of said longitudinal members when said respective one of said longitudinal members is in contact with said fixation surface; and
  a wedge member operable to advance through said thru-hole to urge said respective one of said longitudinal members into engagement with said fixation surface.

14. The system of claim 13, wherein said bridge member is adapted to conform to the anatomy of the spine.

15. The system of claim 14, wherein said bridge member is adjustable to conform to relative orientations of said longitudinal members.

16. The system of claim 13, wherein said bridge member is operatively coupled to one of said engaging members and defines an opening sized to receive an elongated portion operatively coupled to another of said engaging members to provide said adjustable length between said pair of engaging members.

17. The system of claim 16, wherein said elongated portion is adapted to provide further adjustment to said connector.

18. The system of claim 17, wherein said elongated portion includes a reduced cross sectional area, said reduced cross sectional area being deformable to provide said further adjustment to said connector.

19. The system of claim 17, wherein said further adjustment to said connector conforms said elongated portion to the anatomy of the spine.

20. A device for transversely connecting a pair of spinal rods operably engaged to the spine, comprising:
  a pair of engaging members, each including:
    a fixation surface adapted to engage a respective one of the spinal rods thereon and a thru-hole oriented at an oblique angle relative to an axis of the device extending transversely across the pair of spinal rods; and
    a wedge member operable to advance through said thru-hole to urge said respective one of the spinal rods laterally relative to said wedge member and into engagement with said fixation surface; and
  a bridge member adapted to link said pair of engaging members, said bridge member being operatively coupled to one of said engaging members and defining an opening sized to receive an elongated portion operatively coupled to another of said engaging members to provide adjustable length between said engaging members, said elongated portion being adjustable to conform to the anatomy of the spine.

21. The device of claim 20, wherein said bridge member is integrally attached to said one of said engaging members, said opening in said bridge member being a slot extending generally along said axis of the device to provide adjustable length between said engaging members.

22. The device of claim 20, wherein said elongated portion is adjustable to conform to relative orientations of the spinal rods.

23. The device of claim 22, wherein said bridge member includes a reduced cross sectional portion, said reduced cross sectional portion being deformable to conform to misalignments between the spinal rods.

24. The device of claim 20, wherein each of said engaging members includes a receptacle disposed adjacent said fixation surface and configured to receive a respective one of the spinal rods when the engaging members are disposed over the spinal rods.

* * * * *